US008541030B2

(12) United States Patent
Lim et al.

(10) Patent No.: US 8,541,030 B2
(45) Date of Patent: Sep. 24, 2013

(54) PREPARATION METHOD OF SUSTAINED-RELEASE MICROCAPSULES HAVING INITIAL BURST INHIBITING PROPERTY AND THE MICROCAPSULES THEREBY

(75) Inventors: Nak-Hyun Lim, Chungcheongbuk-do (KR); Jung-Kwoun Kim, Gyeongsangnam-do (KR); Hyung-Joon Jung, Chungcheongbuk-do (KR); Se-Yeon Kim, Incheon-si (KR); Goo-Young Jung, Chungcheongbuk-do (KR); Kyung-Hoi Cha, Gyeonggi-do (KR); Mork-Soon Park, Daejeon-si (KR)

(73) Assignee: Dongkook Pharmaceutical Co., Ltd., Seoul (KR)

( * ) Notice: Subject to any disclaimer, the term of this patent is extended or adjusted under 35 U.S.C. 154(b) by 314 days.

(21) Appl. No.: 12/516,275

(22) PCT Filed: Nov. 21, 2007

(86) PCT No.: PCT/KR2007/005892
§ 371 (c)(1),
(2), (4) Date: May 26, 2009

(87) PCT Pub. No.: WO2008/066279
PCT Pub. Date: Jun. 5, 2008

(65) Prior Publication Data
US 2010/0272820 A1    Oct. 28, 2010

(30) Foreign Application Priority Data
Nov. 27, 2006  (KR) .................. 10-2006-0117929

(51) Int. Cl.
*A61K 9/50*  (2006.01)
(52) U.S. Cl.
USPC ..................................................... 424/497
(58) Field of Classification Search
None
See application file for complete search history.

(56) References Cited

U.S. PATENT DOCUMENTS

| | | | |
|---|---|---|---|
| 5,183,662 A | 2/1993 | Morita et al. | |
| 5,639,480 A * | 6/1997 | Bodmer et al. | 424/501 |
| 5,688,530 A * | 11/1997 | Bodmer et al. | 424/501 |
| 5,876,756 A * | 3/1999 | Takada et al. | 424/489 |
| 5,876,761 A * | 3/1999 | Bodmer et al. | 424/501 |
| 6,117,455 A * | 9/2000 | Takada et al. | 424/501 |
| 6,534,094 B2 | 3/2003 | Moyano et al. | |
| 2001/0018072 A1* | 8/2001 | Unger | 424/484 |
| 2002/0039594 A1* | 4/2002 | Unger | 424/426 |
| 2004/0091541 A1* | 5/2004 | Unger | 424/486 |
| 2008/0066741 A1* | 3/2008 | LeMahieu et al. | 128/200.21 |
| 2008/0311162 A1* | 12/2008 | Darmuzey et al. | 424/401 |

FOREIGN PATENT DOCUMENTS

| | | |
|---|---|---|
| JP | 05-004924 | 1/1993 |
| JP | 10-203966 | 8/1998 |
| KR | 10-0194827 | 9/1991 |
| KR | 10-0293882 | 4/1995 |
| KR | 10-0409413 | 4/1997 |
| KR | 10-0442931 | 7/2004 |
| KR | 10-2005-0086708 | 8/2005 |
| WO | WO 93/24150 | 12/1993 |
| WO | WO 2004045633 A2 * | 6/2004 |

OTHER PUBLICATIONS

Pistel KF, Kissel T. Effects of salt addition on the microencapsulation of proteins using W/O/W double emulsion technique. J Microencapsul. Jul.-Aug. 2000;17(4):467-83.*
T Freytag, A Dashevsky, L Tillman, G.E Hardee, R Bodmeier. Improvement of the encapsulation efficiency of oligonucleotide-containing biodegradable microspheres. Journal of Controlled Release vol. 69, Issue 1, Oct. 3, 2000, pp. 197-207.*
Xiaosong Luan, Marc Skupin, Jürgen Siepmann, Roland Bodmeier. Key parameters affecting the initial release (burst) and encapsulation efficiency of peptide-containing poly(lactide-co-glycolide) microparticles. International Journal of Pharmaceutics vol. 324, Issue 2, Nov. 6, 2006, pp. 168-175.*
T. Hino, S. Shimabayashi, M. Tanaka, M. Nakano, H. Okochi. Improvement of encapsulation efficiency of water-in-oil-inwater emulsion with hypertonic inner aqueous phase. Journal of Microencapsulation 2001, vol. 18, No. 1 , pp. 19-28.*
English-language machine translation of: Okada, H. et al., KR 10-0194827, published Sep. 30, 1991 (listed on accompanying Form PTO/SB/08A as (Document FP1).
English-language machine translation of: Igari, Y. et al., KR 10-0409413, published Apr. 28, 1997 (listed on accompanying Form PTO/SB/08A as (Document FP4).
English-language abstract for: Bodmer, D. et al., KR 10-0442931, Korean Patent Abstracts (2004) (listed on accompanying Form PTO/SB/08A as (Document FP5).
English-language abstract for: Lambert, O. et al., KR 10-2005-0086708, Korean Patent Abstracts (2004) (listed on accompanying Form PTO/SB/08A as (Document FP6).
English-language abstract for: Toshiro, B. et al., JP 10-203966, published Sep. 4, 1998 (listed on accompanying Form PTO/SB/08A as (Document FP8).
International Search Report from the Korean Intellectual Property Office for International Appl. No. PCT/KR2007/005892, dated Feb. 26, 2008.
English-language abstract of Korean Patent No. KR 10-0194827 (listed on accompanying Form PTO/SB/08A as Document FP9), Sep. 30, 1991.
English-language abstract of Korean Patent No. KR 10-0293882 (listed on accompanying Form PTO/SB/08A as Document FP10), Apr. 28, 1995.

(Continued)

*Primary Examiner* — Robert A Wax
*Assistant Examiner* — Olga V Tcherkasskaya
(74) *Attorney, Agent, or Firm* — Sterne, Kessler, Goldstein & Fox P.L.L.C.

(57) ABSTRACT

Disclosed is a method for preparing a longer sustained-release formulation containing bioactive substances. More particularly, the present invention provides a method for preparing longer sustained-release microcapsules comprising: adding an emulsion including bioactive substances, biocompatible polymer and polyvinylpyrrolidone to an aqueous solution.

6 Claims, 3 Drawing Sheets

(56) References Cited

OTHER PUBLICATIONS

English-language abstract of Korean Patent No. KR 10-0409413 (listed on accompanying Form PTO/SB/08A as Document FP11), Apr. 28, 1997.

English-language abstract of Korean Patent No. KR 10-0442931 (listed on accompanying Form PTO/SB/08A as Document FP12), Jul. 23, 2004.

English-language abstract of Korean Patent No. KR 10-2005-0086708 (listed on accompanying Form PTO/SB/08A as Document FP13), Aug. 30, 2005.

English-language abstract of Japanese Patent No. JP 05-004924 (listed on accompanying Form PTO/SB/08A as Document FP14), Jan. 14, 1993.

English-language abstract of Japanese Patent No. JP 10-203966 (listed on accompanying Form PTO/SB/08A as Document FP15), Aug. 4, 1998.

* cited by examiner

PREPARATION METHOD OF SUSTAINED-RELEASE MICROCAPSULES HAVING INITIAL BURST INHIBITING PROPERTY AND THE MICROCAPSULES THEREBY

CROSS-REFERENCE TO RELATED APPLICATIONS

This is a 35 U.S.C. §371 National Phase entry of International Application No. PCT/KR2007/005892, filed Nov. 21, 2007, that claims priority to Korean Application No. 10-2006-0117929, filed Nov. 27, 2006.

TECHNICAL FIELD

The present invention relates to preparation method of longer sustained-release microcapsules containing bioactive substances and, more particularly, to a method for preparation of sustained-release microcapsules with excellent initial release inhibitory properties of bioactive substances and microcapsules prepared by the same.

BACKGROUND ART

In the last few decades, there has been a great development of longer sustained-release formulations including biodegradable or biocompatible synthetic polymers as drug delivery materials and bioactive substances, especially, peptides and salts thereof. Such formulations have a plurality of advantages in that they can significantly reduce inconvenience of patients caused by frequently administering the formulations to patients to improve patient compliance, maintain constant concentration of drugs in blood to reduce side effects, and cut down medical expenses.

Korean Patent Reg. No. 10-0442931 disclosed a method for preparation of sustained-release formulations in a microcapsule form, which dissolves polymeric carrier materials in any suitable organic solvent that does not dissolve pharmaceutical compounds, and adds aqueous medium containing excess of protective colloids and phase derivatives to the solution. But, this method requires complicated procedures in manufacturing the formulations and has very low production yield leading to a rise in price of a product.

Korean Patent Laid-Open No. 10-2005-0086708 disclosed a method for preparation of octreotide acetate micro particles of linear poly(lactide-co-glycolide) polymer that contains less than 1% of silicon oil or heptane.

Korean Patent Reg. 10-0194827 disclosed a method for preparation of microcapsules for zero-order releasing of bioactive polypeptides over more than 2 months, which prepares an aqueous oil emulsion that has an inner aqueous phase containing about 20 to 70% (w/w) of polypeptide and an oil phase containing copolymer or homopolymer with a molecular weight of 7,000 to 30,000 and compositional ratio of lactic acid/glycolic acid in the range of 80/10 to 100/0, and forms the emulsion into microcapsules.

Korean Patent Reg. No. 10-0409413 disclosed a method for preparation of microemulsion that comprises preparing the microemulsion by drying-in-water, and heat drying the emulsion at above glass transition temperature (Tg) of biodegradable polymer to considerably inhibit initial release of bioactive substances and to minimize amount of organic solvent used in the method. For this method, there is required above 50% of lactic acid among constitutional ingredients of the biodegradable polymer and Tg of at least 47° C. The method also has a drawback that bioactive substances may be modified by heat.

Korean Patent Reg. No. 10-0293882 disclosed novel salts, a method for preparation of the novel salts comprising cations derived from peptides containing basic groups and anions derived from polyester having carboxyl terminal, and use thereof for production of a sustained-release formulation type composition. However, the use comprises the steps of: freezing and forming drug and polymer into droplets; drying the droplets under vacuum conditions to form a transparent film; dispersing the film in dichloromethane and again drying the dispersion; compressing and molding the dried material; and administering the molded product by means of a syringe needle with relative larger diameter such as 16 or 18 gauge needle, which, therefore, has a problem of causing patients to experience a fear of pain.

DISCLOSURE OF INVENTION

Technical Problem

Accordingly, the present invention is directed to solve the problems described above in regard to conventional methods and an object of the present invention is to provide a method for preparation of a longer sustained-release formulation with excellent initial release inhibitory properties without typically known problems.

Another object of the present invention is to provide a longer sustained-release formulation with excellent initial release inhibitory properties without typically known problems.

Technical Solution

In order to accomplish the above objects, a first aspect of the present invention is to provide a method for preparing longer sustained-release microcapsules comprising: adding an emulsion containing bioactive substances, biocompatible polymer and polyvinylpyrrolidone to an aqueous solution.

According to a second aspect of the present invention, there is provided a method for preparing longer sustained-release microcapsules comprising: adding an emulsion containing bioactive substances and biocompatible polymer to an aqueous solution containing salts.

Hereinafter, the present invention will be described in detail below.

The present invention provides a method for preparing a longer sustained-release formulation with excellent initial release inhibitory properties and the first aspect of the present invention described above is achieved by addition of an emulsion containing bioactive substances, biocompatible polymer and polyvinylpyrrolidone to an aqueous solution.

The bioactive substances are not particularly restricted but preferably include any one selected from peptides and salts thereof, for example, octreotide, lanreotide, goserelin, leuprolide, triptorelin, historelin and desmopressin, etc. and salts thereof such as acid addition salts.

The biocompatible polymer is often called biodegradable polymer and may comprise polymers generally used in pharmaceutical production of microcapsules. For the present invention, the biocompatible polymer preferably includes polylactides, polyglycolides and copolymers thereof such as poly(lactide-co-glycolide). In view of improving initial release inhibitory performance, it is preferably recommended that such biocompatible polymer is combined with glucose. An illustrative example of the polymer combined with glucose for controlling initial release inhibitory properties is disclosed in Korean Patent Reg. No. 10-0442931, the entire contents of which are hereby incorporated by reference into the present invention.

The biocompatible polymer useable in the present invention may include polymers with a weight average molecular weight of 60,000 or less, for example:
poly(lactide-co-glycolide) (50:50) with a molecular weight of 13,000;
poly(lactide-co-glycolide) (50:50) with a molecular weight of 33,000;
poly(lactide-co-glycolide) (50:50) with a molecular weight of 52,000;
poly(lactide-co-glycolide) (75:25) with a molecular weight of 20,000;
poly(lactide) (100:0) with a molecular weight of 16,000, and the like. Such polymers are clearly illustrated by RG502H, RG503H, RG504H, RG752H and R202H, all of which are available from Boehringer Ingelheim GmbH. Polyvinylpyrrolidone used in the method according to the first aspect of the present invention has a role of raising drug encapsulation efficacy and endowing initial release inhibitory properties of the drug in the formulation. Considering the drug encapsulation efficacy and the initial drug release inhibitory properties, content of polyvinylpyrrolidone is preferably ranged from 0.01 to 5.0 w/w % relative to total weight of drug, biocompatible polymer and polyvinylpyrrolidone.

Salts useable in the method according to the second aspect of the present invention can improve encapsulation efficacy of bioactive substances and initial release inhibitory properties of the bioactive substances in the formulation and preferably comprise, for example, sodium chloride (NaCl), potassium chloride (KCl), ammonium chloride ($NH_4Cl$), magnesium sulfate ($MgSO_4$), sodium hypochlorite (NaClO), sodium nitrate ($NaNO_3$) and the like. Amount of the salts to be added is preferably ranged from 0.02 to 0.15M in view of the encapsulation efficacy and the initial release inhibitory properties of the bioactive substances.

The method for preparing a longer sustained-release formulation with excellent initial release inhibitory properties of bioactive substances according to the first aspect of the present invention comprises the steps of:

(a) preparing an emulsion by mixing a non-aqueous solution 1 containing bioactive substances with another non-aqueous solution 2 containing biocompatible polymer and polyvinylpyrrolidone; and (b) adding the emulsion prepared by step (a) to an aqueous solution to form microcapsules.

The non-aqueous solution 1 used in step (a) contains a solvent which is not particularly limited so far as it can dissolve the bioactive substances to be used and is preferably selected from, for example, methanol, ethanol, propanol, benzyl alcohol, acetic acid and hydrochloric acid.

The non-aqueous solution 2 used in step (a) contains a solvent which is not particularly limited so far as it can dissolve the biocompatible polymer and polyvinylpyrrolidone and is preferably selected from, for example, methylene chloride, chloroform, acetonitrile, dimethylsulfoxide, dimethylformamide and ethyl acetate.

Mixing and vigorously agitating the non-aqueous solution 1 and non-aqueous solution 2 for several minutes to several tens minutes results in a transparent emulsion.

The aqueous solution used in step (b) for producing microcapsules is a continuous phase to which the prepared emulsion is added, and may further contain a desired surfactant. Illustrative examples of the surfactant include polyvinyl alcohol, Poloxamer 407, polyethyleneglycol 4000, Arlacel 165, glycerin and/or propyleneglycol, etc. Such surfactant raises the encapsulation efficacy of bioactive substances. Amount of the surfactant added to the aqueous solution is preferably up to 5.0% (w/v) relative to volume of the aqueous solution and, if exceeding this amount, there may be a reduction of the encapsulation efficacy of drug.

Microcapsules formulated by the above procedures can improve the encapsulation efficacy of drug, that is, the bioactive substances and endow zero-order release properties free of initial drug release to the formulation, regardless of molecular weight of biocompatible polymer and/or content of lactides.

The method for preparing a longer sustained-release formulation with excellent initial release inhibitory properties of bioactive substances according to the second aspect of the present invention comprises the steps of:

(a') preparing an emulsion by mixing a non-aqueous solution 1 containing bioactive substances with another non-aqueous solution 2 containing biocompatible polymer; and (b') adding the emulsion prepared by step (a') to an aqueous solution containing salts to form microcapsules with longer sustained-release properties.

The non-aqueous solution 1 used in step (a') is prepared using a solvent which is not particularly limited so far as it can dissolve the bioactive substances to be used and is preferably selected from, for example, methanol, ethanol, propanol, benzyl alcohol, acetic acid and hydrochloric acid.

The non-aqueous solution 2 used in step (a') is prepared using a solvent which is not particularly limited so far as it can dissolve the biocompatible polymer, and is preferably selected from, for example, methylene chloride, chloroform, acetonitrile, dimethylsulfoxide, dimethylformamide and ethyl acetate.

Mixing and vigorously agitating the non-aqueous solution 1 and non-aqueous solution 2 for several minutes to several tens of minutes results in a transparent emulsion.

The aqueous solution used in step (b') for producing microcapsules is a continuous phase to which the prepared emulsion is added, and may further contain a desired surfactant. Illustrative examples of the surfactant include polyvinyl alcohol, Poloxamer 407, polyethyleneglycol 4000, Arlacel 165, glycerin and/or propyleneglycol, etc. Such surfactant raises the encapsulation efficacy of bioactive substances. Amount of the surfactant added to the aqueous solution is preferably up to 5.0% (w/v) relative to volume of the aqueous solution and, if exceeding this amount, there may be a reduction of the encapsulation efficacy of drug.

Salts added to the aqueous solution in step (b') can raise the encapsulation efficacy of drug and effectively inhibit initial release efficacy of drug. That is, microcapsules formulated by the above procedures can improve the encapsulation efficacy of drug, that is, the bioactive substances and endow zero-order release properties free of initial drug release to the formulation, regardless of molecular weight of biocompatible polymer and/or content of lactides.

Microcapsules formulated according to the first and second aspects of the present invention maintain drug concentration of above 3 ng/ml until 28 days after administration to animals, although they show different patterns of drug concentration in blood. Accordingly, the inventive microcapsules can be formulated into longer sustained-release formulations having a release period of more than 1 month.

Advantageous Effects

According to the present invention, there are provided a method for preparing a longer sustained-release formulation containing bioactive substances such as peptides and salts thereof and, more particularly, a longer sustained-release formulation with excellent initial release inhibitory properties of the bioactive substances.

BRIEF DESCRIPTION OF THE DRAWINGS

The above objects, features and advantages of the present invention will become more apparent to those skilled in the related art in conjunction with the accompanying drawings. In the drawings.

BEST MODE FOR CARRYING OUT THE INVENTION

Figure 1:
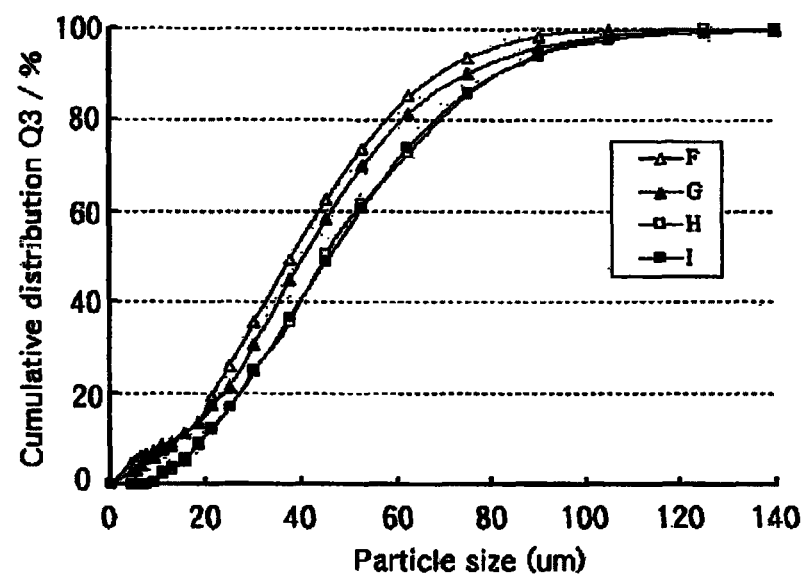
FIG. 1 shows results of an experiment for determining particles size distributions of microcapsules formulated according to the present invention.

Hereinafter, the present invention will be described in detail from the following preferred examples with reference to the accompanying drawings. However, these are intended to illustrate the invention as preferred embodiments of the present invention and do not limit the scope of the present invention.

Comparative Example

Preparation of Microcapsules by Generally Known Oil-In-Water Emulsification Method 0.15 g of octreotide acetate (GMP grade) was dissolved in methanol based on contents listed in Table 1 and Table 2, while 1.85 g of biocompatible polymer was dissolved in methylene chloride. Both of the organic solvent phases were mixed together under vigorous agitation for 10 minutes to prepare a transparent emulsion (DP, dispersion phase). The emulsion was slowly dropped to a water-soluble solution containing 0.5% polyvinyl alcohol (Mw=30,000 to 70,000, Sigma) at 25° C. while vigorously agitating the solution by means of a L4R mixer (Silverson). After 10 minutes, the temperature was raised to 41° C. and the agitation speed was decreased to evaporate organic solvent moiety for 2 hours. Thereafter, in order to solidify the microcapsules, the emulsion was cooled for 30 minutes while keeping the temperature at 25° C. The cooled microcapsules underwent vacuum filtration using a cellulose filter with pore size of 5.0☐, followed by washing the filtrate with distilled water three times and vacuum drying at room temperature for 48 hours.

Comparative Example 1

Preparation of Microcapsules Containing Octreotide by Using Biocompatible Polymers with Different Inherent Viscosity

TABLE 1

| Formulation | Bio-compatible polymer | Methanol (g) | Methylene chloride (g) | Drug encapsulation efficacy(%) |
|---|---|---|---|---|
| A | RG502H[1] | 1.08 | 4.32 | 4.5 |
| B | RG503H[2] | 1.63 | 7.40 | 4.7 |
| C | RG504H[3] | 2.14 | 9.71 | 4.9 |

[1]lactide:glycolide = 50:50, available from Boehringer Ingelheim, i.v. = 0.20 dl/g, Resomer ™
[2]lactide:glycolide = 50:50, available from Boehringer Ingelheim, i.v. = 0.39 dl/g, Resomer ™
[3]lactide:glycolide = 50:50, available from Boehringer Ingelheim, i.v. = 0.52 dl/g, Resomer ™

Comparative Example 2

Preparation of Formulations Using Biocompatible Polymers with Different Lactide/Glycolide Compositions

TABLE 2

| Formulation | Bio-compatible polymer | Methanol (g) | Methylene chloride (g) | Drug encapsulation efficacy(%) |
|---|---|---|---|---|
| A | RG502H[1] | 1.08 | 4.32 | 4.5 |
| D | RG752H[2] | 1.39 | 5.50 | 4.2 |
| E | R202H[3] | 1.64 | 6.56 | 4.1 |

[1]lactide:glycolide = 50:50, available from Boehringer Ingelheim, i.v. = 0.20 dl/g, Resomer ™
[2]lactide:glycolide = 75:25, available from Boehringer Ingelheim, i.v. = 0.20 dl/g, Resomer ™
[3]lactide:glycolide = 100:0, available from Boehringer Ingelheim, i.v. = 0.20 dl/g, Resomer ™

Example 1

Preparation of Microcapsules by Mixing Biocompatible Polymer and Excipient in Organic Solvent Phase (DP)

(i) Preparation of Formulation by Mixing RG502H with PVP-17PF (when Batch Size is 2.0 g, Content of PVP-17PF is Ranges from 0.5 to 5.0%)

0.15 g of octreotide acetate was dissolved in 1.08 g of methanol and biocompatible polymer and polyvinylpyrrolidone were dissolved in 4.32 g of methylene chloride with contents listed in the following Table 3. Both of the organic solvent phases were mixed together under vigorous agitation for 10 minutes to prepare a transparent emulsion. Subsequent procedures were performed in the same manner as described in the above comparative examples.

TABLE 3

| Formulation | RG502H[1] (g) | PVP-17PF[2] (g) | Drug encapsulation efficacy(%) |
|---|---|---|---|
| F | 1.84 | 0.01 | 5.1 |
| G | 1.83 | 0.02 | 5.7 |
| H | 1.80 | 0.05 | 5.3 |
| I | 1.75 | 0.10 | 4.7 |

[1]lactide:glycolide = 50:50, available from Boehringer Ingelheim, i.v. = 0.20 dl/g, Resomer ™
[2]BASF, Kollidon ™

(ii) Preparation of Formulation by Mixing RG752H with PVP-17PF (when Batch Size is 2.0 g, Content of PVP-17PF is Ranges from 0.5 to 5.0%)

0.15 g of octreotide acetate was dissolved in 1.39 g of methanol and a biocompatible polymer and polyvinylpyrrolidone were dissolved in 5.50 g of methylene chloride according to contents listed in the following Table 4. Both of the organic solvent phases were mixed together under vigorous agitation for 10 minutes to prepare a transparent emulsion. Subsequent procedures were performed in the same manner as described in the above comparative examples.

TABLE 4

| Formulation | RG752H(g) | PVP-17PF(g) | Drug encapsulation efficacy(%) |
|---|---|---|---|
| J | 1.84 | 0.01 | 5.3 |
| K | 1.83 | 0.02 | 5.7 |
| L | 1.80 | 0.05 | 5.5 |
| M | 1.75 | 0.10 | 5.0 |

Example 2

Preparation of Microcapsules by Varying Concentration of Polyvinyl Alcohol in Water Phase (CP)

(i) Preparation of Formulation by Mixing RG502H with PVP-17PF 0.15 g of octreotide acetate was dissolved in 1.08 g of methanol while 1.83 g of RG502H and 0.02 g of polyvinylpyrrolidone were dissolved in 4.32 g of methylene chloride. Both of the organic solvent phases were mixed together under vigorous agitation for 10 minutes to prepare a transparent emulsion. Subsequent procedures were performed in the same manner as described in the above comparative examples and concentration of polyvinyl alcohol in the water phase was listed in the following Table 5.

TABLE 5

| Formulation | Concentration of polyvinyl alcohol (%) | Drug encapsulation efficacy(%) |
|---|---|---|
| N | 0.1 | 5.0 |
| G | 0.5 | 5.7 |
| O | 1.0 | 5.6 |
| P | 5.0 | 4.9 |

(ii) Preparation of Formulation by Mixing RG752H with PVP-17PF 0.15 g of octreotide acetate was dissolved in 1.39 g of methanol while 1.83 g of RG752H and 0.02 g of polyvinylpyrrolidone were dissolved in 5.50 g of methylene chloride. Both of the organic solvent phases were mixed together under vigorous agitation for 10 minutes to prepare a transparent emulsion. Subsequent procedures were performed in the same manner as described in the above comparative examples and concentration of polyvinyl alcohol in the water phase was listed in the following Table 6.

TABLE 6

| Formulation | Concentration of polyvinyl alcohol(%) | Drug encapsulation efficacy(%) |
|---|---|---|
| Q | 0.1 | 5.2 |
| K | 0.5 | 5.7 |
| R | 1.0 | 5.6 |
| S | 5.0 | 5.0 |

Example 3

Preparation of Microcapsules by Using Salts as Additive in Water Phase (CP)

(i) Preparation of Formulation Using RG502H 0.15 g of octreotide acetate was dissolved in 1.08 g of methanol while 1.83 g of RG502H was dissolved in 4.32 g of methylene chloride. Both of the organic solvent phases were mixed together under vigorous agitation for 10 minutes to prepare a transparent emulsion. Subsequent procedures were performed in the same manner as described in the above comparative examples and concentration of sodium chloride in the water phase was listed in the following Table 7.

| Formulation | Sodium chloride (mole) | Drug encapsulation efficacy(%) |
|---|---|---|
| A | 0 | 4.5 |
| T | 0.02 | 5.2 |
| U | 0.15 | 5.6 |
| V | 0.5 | 3.9 |

(ii) Preparation of Formulation Using RG752H 0.15 g of octreotide acetate was dissolved in 1.08 g of methanol while 1.83 g of RG752H was dissolved in 4.32 g of methylene chloride. Both of the organic solvent phases were mixed together under vigorous agitation for 10 minutes to prepare a transparent emulsion. Subsequent procedures were performed in the same manner as described in the above comparative examples and concentration of sodium chloride in the water solution phase was listed in the following Table 8.

TABLE 8

| Formulation | Sodium chloride (mole) | Drug encapsulation efficacy(%) |
|---|---|---|
| D | 0 | 4.2 |
| W | 0.02 | 4.9 |
| X | 0.15 | 5.9 |
| Y | 0.5 | 4.1 |

Experimental Example

Evaluation of Characteristics of Microcapsules (i) Particle Size Distribution

About 100 mg of microcapsules formulated in each of the above examples were suspended in 50 ml of distilled water. While agitating the suspension to prevent precipitation of the microcapsules, the suspension was subjected to detection of turning patterns using a He—Ne laser source at 632 nm and determination of a particle size distribution. From results of the determination as shown in FIG. 1, it was identified that the distribution of fine microcapsules with diameter of lesser than 20□ was reduced as the content of polyvinylpyrrolidone was increased.

(ii) Morphology of Microcapsules

In order to observe appearance of microcapsules, about 50 mg of microcapsules were fixed to an aluminum stub, coated with platinum for 15 minutes under vacuum degree of 0.1 torr and high voltage (10 kV), mounted on a SEM main body, and monitored for morphology of microcapsules using an image analysis program.

Figure 2:
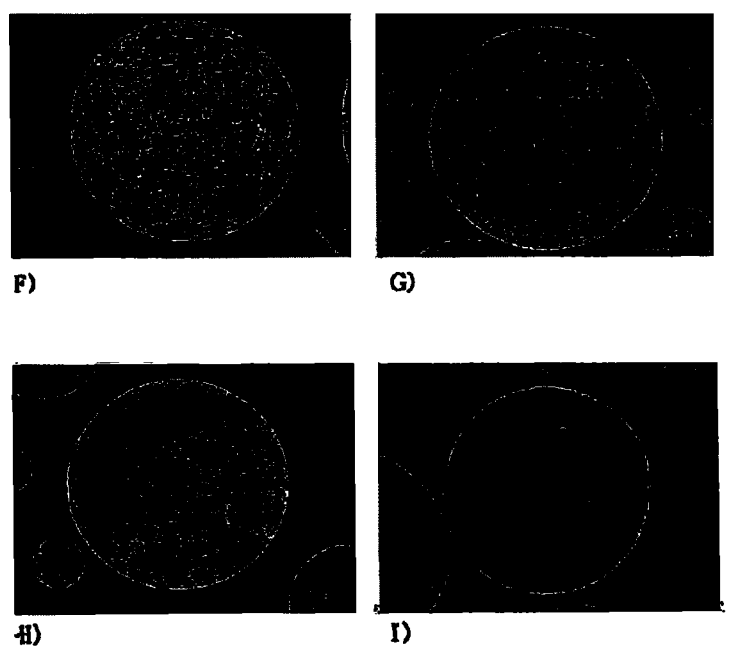
FIG. 2 shows results of an experiment for determining morphology of microcapsules formulated according to the present invention.

From results of the determination as shown in FIG. 2, it was identified that porosity of the microcapsules was reduced as the content of polyvinylpyrrolidone was increased.

(iii) Determination of Encapsulation Efficacy of Octreotide

After completely dissolving about 100 mg of microcapsules in 25 ml of tetrahydrofuran, 75 ml of 0.1M acetate buffer (pH 4.0) was added to the solution for extraction of octreotide into an aqueous phase. After filtering the extract through a syringe filter having a size of 0.45□, content of octreotide encapsulated in the microcapsules was measured using HPLC. The used HPLC adapted YMC C-18 ODS (4.6×150 mm) as a column, amount of a sample injected into the column was 20□ and detection wavelength was 210 nm. As a mobile phase, 0.1% TFA in water (a) and 0.1% TFA in acetonitrile (b) were used, respectively, and concentration gradient of the mobile phase was as follows: 0 to 20 minutes; 15% to 70% (B), 20.1 to 30 minutes; 15% (B).

Figure 3:
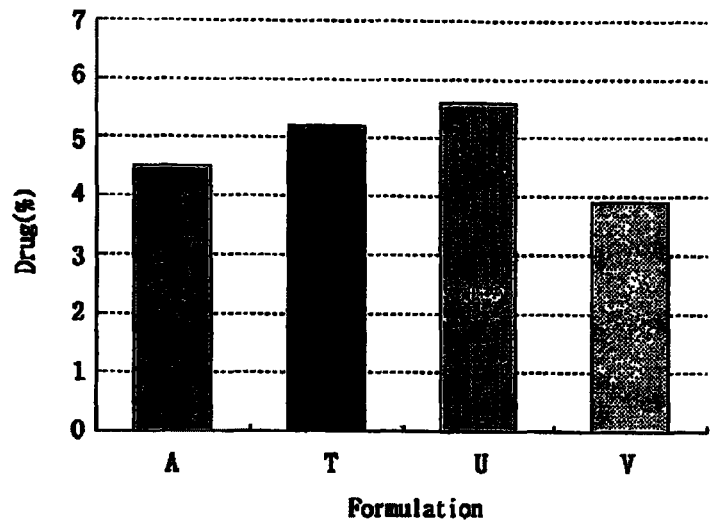
FIG. 3 shows results of an experiment for determining octreotide encapsulation efficacy of microcapsules formulated according to the present invention.

From results of the determination as shown in FIG. 3, it was identified that the drug encapsulation efficacy was increased as the concentration of sodium chloride was increased, however, in case when the concentration was 0.5M, the drug encapsulation efficacy was rather reduced.

(iv) In-Vitro Long Term Release Test

About 50 mg of the formulated microcapsules were placed in a 12 ml test tube and rotated at 25 rpm in 10 ml of 0.033M phosphoric buffer saline (PBS, pH 7.0). After incubated at 37° C., supernatant was take from the test tube at a desired measurement time, centrifuged and analyzed by HPLC.

Figure 4:
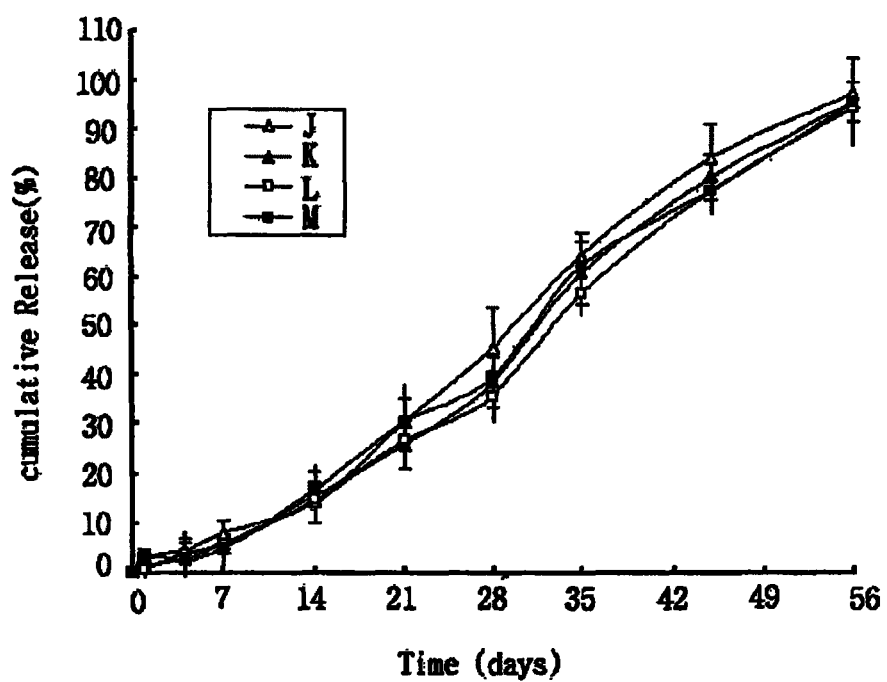
FIG. 4 shows results of in-vitro long term release test of microcapsules formulated according to the present invention.

From results of the measurement as shown in FIG. 4, it was identified that initial release efficacy was very small and zero-order release properties was observed for at least 1 month.

(v) In-Vivo Pharmacokinetic Profile (1) Experimental Material

Rabbit, mannitol, benzyl alcohol, sodium carboxymethyl cellulose, heparin, centrifuge, micropipette, syringe (2) Serum Level of Octreotide To determine the serum drug, microcapsules were injected i.m. into rabbit after dispersing the microparticle in 1.5 ml of vehicle at a dose 5 mg/kg of drug. At 1, 3, 6 and 12 hours and 1, 2, 4, 7, 14, 21, 28, 35, 42 and 49 days, blood samples were taken from each rabbit in amount of 2 ml per case, respectively. The taken blood samples were heparinized, followed by centrifugation at 4° C. for 10 minutes and separation of supernatant from each of the samples. Subsequently, after removing protein moiety from plasma, concentration of octreotide in serum was measured using LC/MS/MS.

Figure 5:
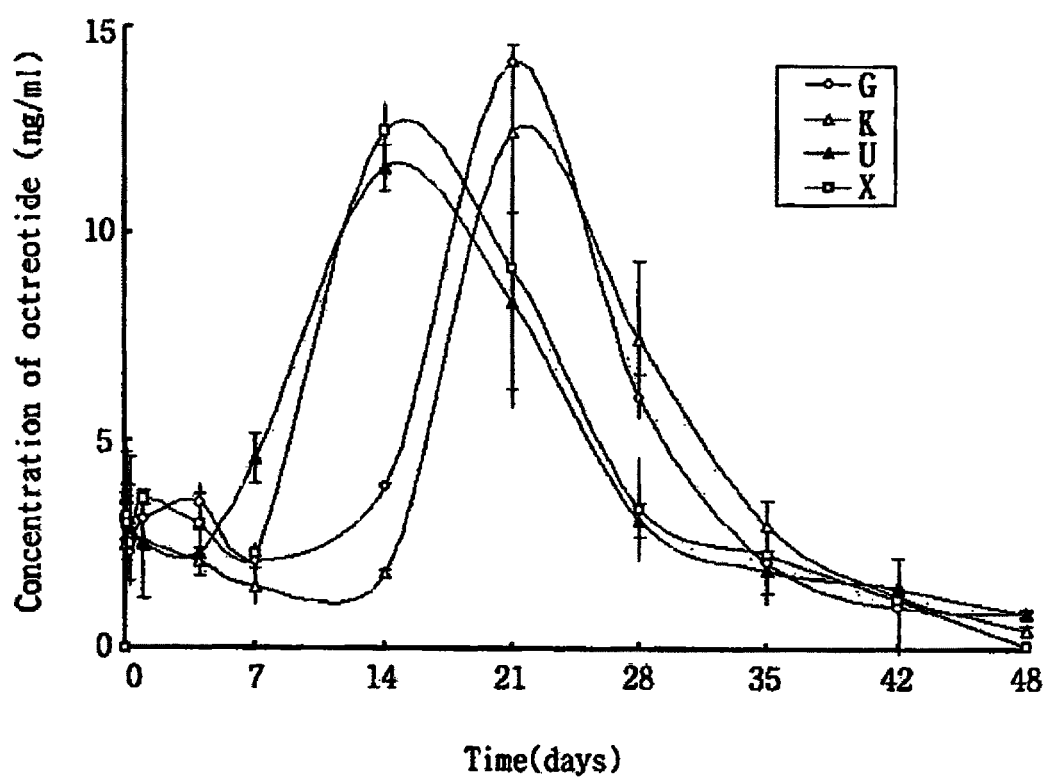
FIG. 5 shows results of an in-vivo pharmacokinetic profiles of microcapsules formulated according to the present invention.

From results of the measurement as shown in FIG. 5, it was identified that the microcapsules formulated according to the present invention can appropriately control octreotide concentration in blood, in case that the drug is released into the blood.

INDUSTRIAL APPLICABILITY

As described in detail above, the present invention provides a method for preparing a longer sustained-release formulation containing bioactive substances such as peptides and salts thereof and, more particularly, a formulation with excellent initial release inhibitory properties.

While the present invention has been described with reference to the accompanying drawings, it will be understood by those skilled in the art that various modifications and variations may be made therein without departing from the scope of the present invention as defined by the appended claims.

The invention claimed is:

1. A method for preparing sustained-release microcapsules comprising: adding an emulsion containing octreotide or a salt thereof as a bioactive substance, a bio-compatible polymer and polyvinylpyrrolidone to an aqueous solution containing a salt in an amount of 0.02 to 0.15 M to provide the sustained-release microcapsules, wherein the salt is sodium chloride, and wherein the drug encapsulation efficacy of the sustained-release microcapsules is increased in an amount of 15.6% to 40.5% compared to that of a sustained-release microcapsules prepared by an aqueous solution not containing salt.

2. The method of claim 1, wherein the emulsion is prepared by mixing a first non-aqueous solution containing the octreotide or a salt thereof and a second non-aqueous solution containing a bio-compatible polymer and polyvinylpyrrolidone.

3. The method of claim 1, wherein the bio-compatible polymer is polylactide-co-glycolide or poly(lactide-co-glycolide)glucose.

4. The method of claim 1, wherein the bio-compatible polymer has an average molecular weight of 60,000 or less.

5. The method of claim 2, wherein the first non-aqueous solution contains methanol.

6. The method of claim 2, wherein the second non-aqueous solution contains methylene chloride.

* * * * *